United States Patent [19]
Hashimoto et al.

[11] Patent Number: 5,849,246
[45] Date of Patent: Dec. 15, 1998

[54] APPARATUS FOR SPRAY STERILIZATION AND METHOD THEREFOR

[75] Inventors: Toshitaka Hashimoto, Naruto; Yoshikane Fukuda, Amagasaki; Ryuichi Tsutsumi, Hirakata, all of Japan

[73] Assignees: Otsuka Pharmaceutical Factory, Inc., Tokushima-ken; Hisaka Works Limited, Osaka, both of Japan

[21] Appl. No.: 635,881

[22] PCT Filed: Aug. 21, 1995

[86] PCT No.: PCT/JP95/01651
§ 371 Date: Jul. 23, 1996
§ 102(e) Date: Jul. 23, 1996

[87] PCT Pub. No.: WO96/05868
PCT Pub. Date: Feb. 29, 1996

[30] Foreign Application Priority Data

Aug. 24, 1994  [JP]  Japan .................................. 6-199158

[51] Int. Cl.⁶ ........................................................ A61L 2/06
[52] U.S. Cl. ............................................. 422/26; 422/307
[58] Field of Search ........................................ 422/26, 307

[56] References Cited

FOREIGN PATENT DOCUMENTS

| | | |
|---|---|---|
| 60-9451 | 3/1985 | Japan . |
| 3-3197 | 1/1991 | Japan . |
| 3-25787 | 6/1991 | Japan . |
| 3-47646 | 10/1991 | Japan . |
| 3-47647 | 10/1991 | Japan . |
| 3-47648 | 10/1991 | Japan . |

*Primary Examiner*—James Ketter
*Attorney, Agent, or Firm*—Sughrue, Mion, Zinn, Macpeak & Seas, PLLC

[57] ABSTRACT

A plurality of stacked trays 2 are accommodated within a rotary housing 3 rotatably supported in a sterilization vessel 1 (FIG. 7a). A medium support port 42a is sealingly engaged with an inlet port 25. Then, a flow of hot water is supplied to the inlet port 25. Thus, a spray hot water is ejected from spray nozzle 23 for heat sterilizing products on the trays 2. Thereafter, a spray of cooling water is ejected from the spray nozzle 23 for cooling the products. The rotary housing 3 is rotated to a position in which inclination of the trays 2 exceeds 90 degrees. Then, the rotary housing 3 is counter-rotated to a position in which the trays 2 are inclined at a vertical orientation (FIG. 7b). A hot gas supply port 37a is sealingly engaged with the inlet port 25 so as to supply a flow of hot air into the inlet port 25, whereby the products may be dried.

4 Claims, 6 Drawing Sheets

APPARATUS FOR SPRAY STERILIZATION AND METHOD THEREFOR

BACKGROUND OF THE INVENTION

1. Field of the Invention

This invention relates to a spray sterilization apparatus for spraying hot water or steam upon containers filled with food or medicine, such as retort pouches or transfusion bags, for sterilization thereof and a method therefor.

2. Description of the Prior Art

In a process for producing retort-packed foods, a quantity of material or food Is filled into a retort-container and the container is sealed. Then, the container is placed in a sterilization apparatus for heat-sterilization.

There are various kinds of sterilization apparatuses for use in such application. One apparatus is of a spray type. In a typical sterilization apparatus of a spray type as shown in FIG. 8, a plural stages of trays 2 (stacked trays) each mounting thereon a product 45 are accommodated within a sterilization vessel 1. A plurality of sprays 23 are mounted in the sterilization vessel, each spray being directed toward a gap between the stacked trays 2. A spray of hot water or steam is ejected from each of the spray nozzles for heat-sterilizing the products. Then, a spray of cooling water is ejected from each of the spray nozzles 23 for cooling the products 45 (refer to for example Japanese Utility Model Publication No. 3-33197).

After completion of the cooling operation, the retort-packed products are removed from the sterilization vessel 1 and transferred to a drying station. In this station, the products are dried in order to eliminate water droplets on the surfaces of the products. Then, the products are transferred to a subsequent station, such as an inspection station or packaging station.

As mentioned in above, prior art installation was equipped with a sterilization apparatus and a dewatering/drying apparatus separately. This required a relatively large floor space for the production line, thus hindering effective utilization of space. It is also noted that wet products were supplied from the sterilization apparatus, so that provision of a drainage pan or a drainage trough before the drying apparatus was needed, for the treatment of water remaining on the products. This invited complication of peripheral constructions. It is further noted that such wet products tended to adhere thereon foreign materials in circulating air, thus causing hygienical problems.

When the products are required of a very high degree of hygienity, such as the case of medical transfusion bags, it is necessary for such products to be sterilized and dried in a clean room. It is noted, however, that, if the sterilization apparatus, as well as the drying apparatus, is provided in a clean room, an increased volume of clean room is required, so as to cause initial costs and running costs, including construction cost, air-conditioning cost, maintenance cost and labor cost, to be significantly increased.

When the trays are removed from the sterilization vessel and directly transferred into the drying apparatus, the contact surfaces between the trays and the products are insufficiently dried.

SUMMARY OF THE INVENTION

The invention is aimed at the provision of a spray sterilization apparatus which permits effective utilization of space and simplification of peripheral constructions, while at the same time maintaining a high degree of hygienity.

The invention is also directed to assuring the contact surfaces between the trays and products to be dried.

In order to achieve the above objects, the apparatus of the invention includes a sterilization vessel of a cylindrical configuration; a rotary housing supported within the sterilization vessel for rotatable movement about a horizontal axis of rotation, the rotary housing accommodating therein a plurality of stacked trays, each of the trays being adapted to mount thereon at least one product; a rotary drive unit for reversibly rotating the rotary housing; a plurality of spray nozzles within the rotary housing, each of the spray nozzles being arranged to be directed to a space between the stacked trays; an inlet port in the rotary housing, the inlet port being in communication with each of the spray nozzles; a medium supply port and a hot gas supply port in the sterilization vessel, the medium supply port and the hot gas supply port being arranged in a plane containing the locus of revolution of the inlet port and spaced apart from one another, so as to be sealingly engageable with the inlet port; means for supplying a flow of hot gas to the hot gas supply port; and means for discharging the hot gas flow having been introduced into the rotary housing from the sterilization vessel. The inlet port is sealingly engaged with the medium supply port while the trays are maintained at a horizontal orientation, so that heating medium and the cooling medium, in this order, may be supplied to the medium supply port; then, the rotary housing is rotated so as to cause the trays to be maintained at a vertical orientation; the inlet port is sealingly engaged with the hot gas supply port, so that hot gas may be supplied from the hot gas supplying means into the rotary housing; and the hot gas is discharged from the sterilization vessel by means of the hot gas discharging means.

Preferably, the rotary housing is adapted to be rotatable to a position in which the trays are inclined beyond the vertical orientation.

The method of the invention includes: accommodating a plurality of trays having a product thereon in a stacked manner within a rotary housing disposed in a sterilization vessel of a cylindrical configuration; injecting a spray of heating medium from a spray nozzle in the rotary housing toward the trays for heat sterilizing the products on the trays, while the trays are maintained at a horizontal orientation; injecting a spray of cooling medium from the spray nozzle for cooling the products, while the trays are maintained at a horizontal orientation; rotating the rotary housing so as to cause the trays to be maintained at a vertical orientation: and supplying hot air from the spray nozzle, while discharging the hot air from the sterilization vessel.

It is preferable to include the steps of, after performing the cooling step subsequent to the heat sterilizing step, rotating the rotary housing to a position in which the trays are inclined further beyond the vertical orientation, maintaining the position for a predetermined period of time, and then, rotating the rotary housing so that the trays are returned to the vertical orientation for performing the drying operation by means of the hot gas.

Operation of the apparatus of the invention is as follows. The inlet port is sealingly engaged with the medium supply port, while the trays are maintained at a horizontal orientation. Thus, a flow of heating medium is introduced from the medium supply port into the inlet port, whereby a spray of heating medium is ejected from each spray nozzle. The sprayed heating medium is diffused in a gap between the stacked trays to heat-sterilize the products on the trays. Then, a flow of cooling medium is supplied to the medium supply port, while the trays are maintained at a horizontal orientation. Thus, a spray of the cooling medium through the inlet port is ejected from each spray nozzles, so as to cause the products on the trays to be cooled to a predetermined temperature. After completion of cooling operation, the rotary housing is rotated to a position in which the trays are maintained at a vertical orientation. Then, the inlet port is sealingly engaged with the hot air supply port, so as to cause the hot air to be supplied from the hot air supply means into the hot air supply ports. Thus, the hot air is ejected from the spray nozzles, whereby cooling medium adhered to the products and the trays are dried. When the hot air is ejected from the spray nozzle, such ejected hot air is evenly distributed throughout the gaps between the trays, since the spray nozzles having been rotated in unison with the rotary housing are directed toward a respective gap between the adjoining trays. The spent hot air having passed through the gaps is exhausted through the discharging means into the atmospheric air. When the trays are maintained at a vertical orientation during drying operation, most of the medium adhered to the products and trays will flow downwardly therefrom (dewatering effect), so that drying time may be reduced.

When the rotary housing is further rotated to a position in which the trays are inclined beyond the vertical orientation (over-hanging), after completion of the cooling operation, the trays become crumbled so that the lower surfaces of the products and the surfaces of the trays are separated from one another. By maintaining such condition for a predetermined period of time, the medium remaining on the contact surfaces between the products and the trays is thermally dried. The rotary housing is counter-rotated to a position in which the trays are returned to the vertical position, to perform the drying operation by ejecting hot air. By this, the trays and the products may be dried more completely.

In accordance with the present apparatus, the sterilization operation and the drying operation may be in a single apparatus., so that miniaturization of the sterilization/drying line, as well as effective utilization of space, may be achieved. Since the products in dry state may be obtained from the sterilization vessel, any countermeasures external to the sterilization vessel, such as a drainage pan or drainage trough, may be obviated, thus achieving simplification of the peripheral construction. Since foreign materials in the atmospheric air are not easily adhered to the products when the products are removed from the apparatus after completion of sterilization, it is possible for the products to be maintained at a high hygienical condition.

When the sterilization/drying line is disposed within a clean room, it is possible to use a relatively small clean room, thus saving on the initial cost and running cost, whereby production cost may be advantageously reduced.

When the drying process is performed while maintaining the trays at a vertical orientation, drying time may be reduced due to the dewatering effect.

When the rotatable housing is rotated to a position in which the trays are inclined at an angle beyond the vertical orientation, after completion of the heat-sterilization operation, it is possible for heating medium remaining on the contact surfaces between the products and the trays may be thermally dried more completely, so that the products may be evenly dried in their entirety.

BEST MODE FOR CARRYING OUT THE INVENTION

The construction of the apparatus of the invention will be explained below with reference to FIGS. 1 through 7.

Figure 1:
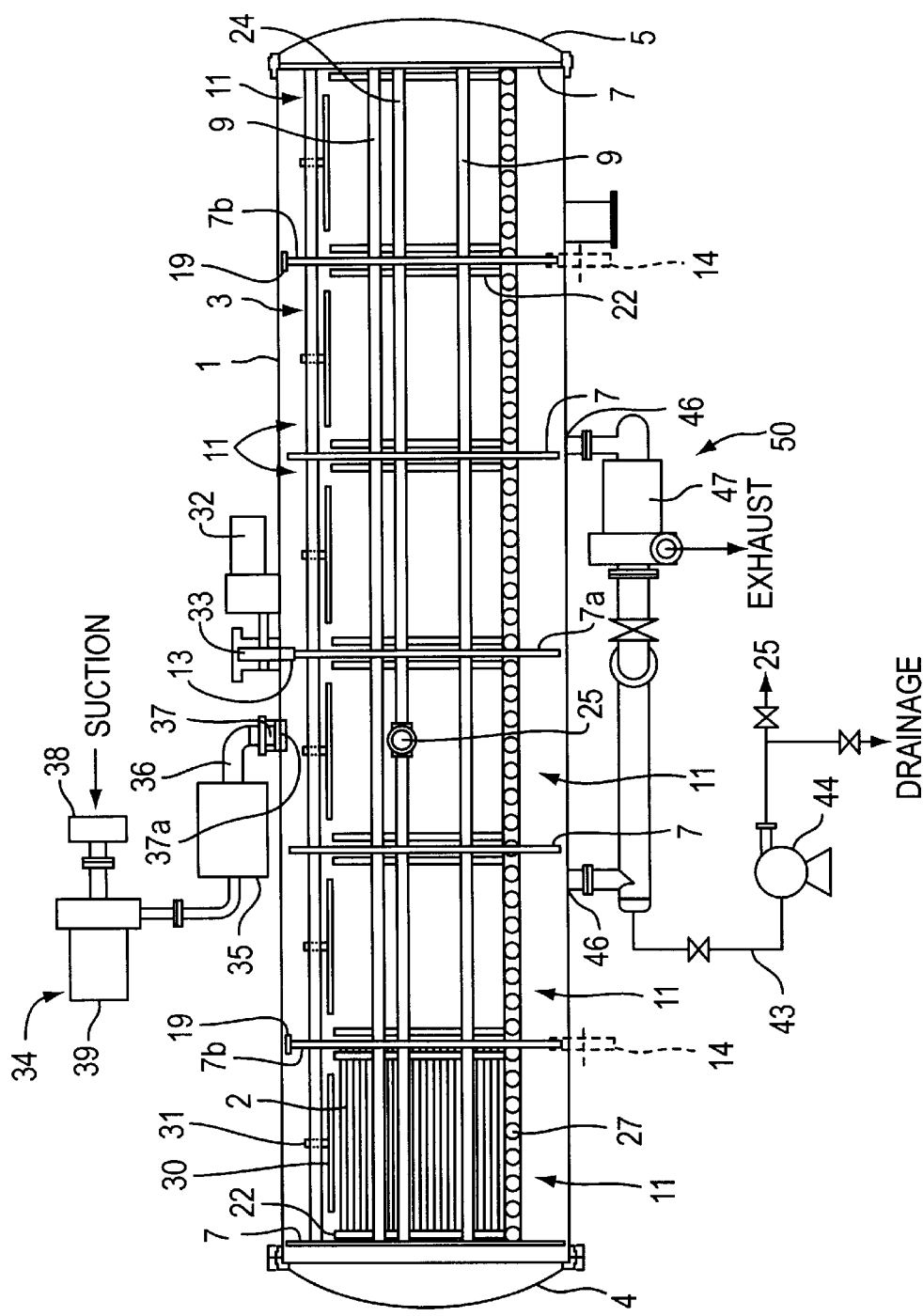
FIG. 1 is a cross-sectional view illustrating the entire construction of an apparatus according to the invention.

As shown in FIG. 1, the apparatus of the invention includes a sterilization vessel 1 of a cylindrical configuration and a rotary housing 3 disposed therein for accommodating therein a plurality of stacked trays 2. The opposite openings of the sterilization vessel 1 at the inlet side (left-hand side in the drawing) and the outlet side (right-hand side) thereof are closed by respective openable closures 4 and 5.

Figure 2:
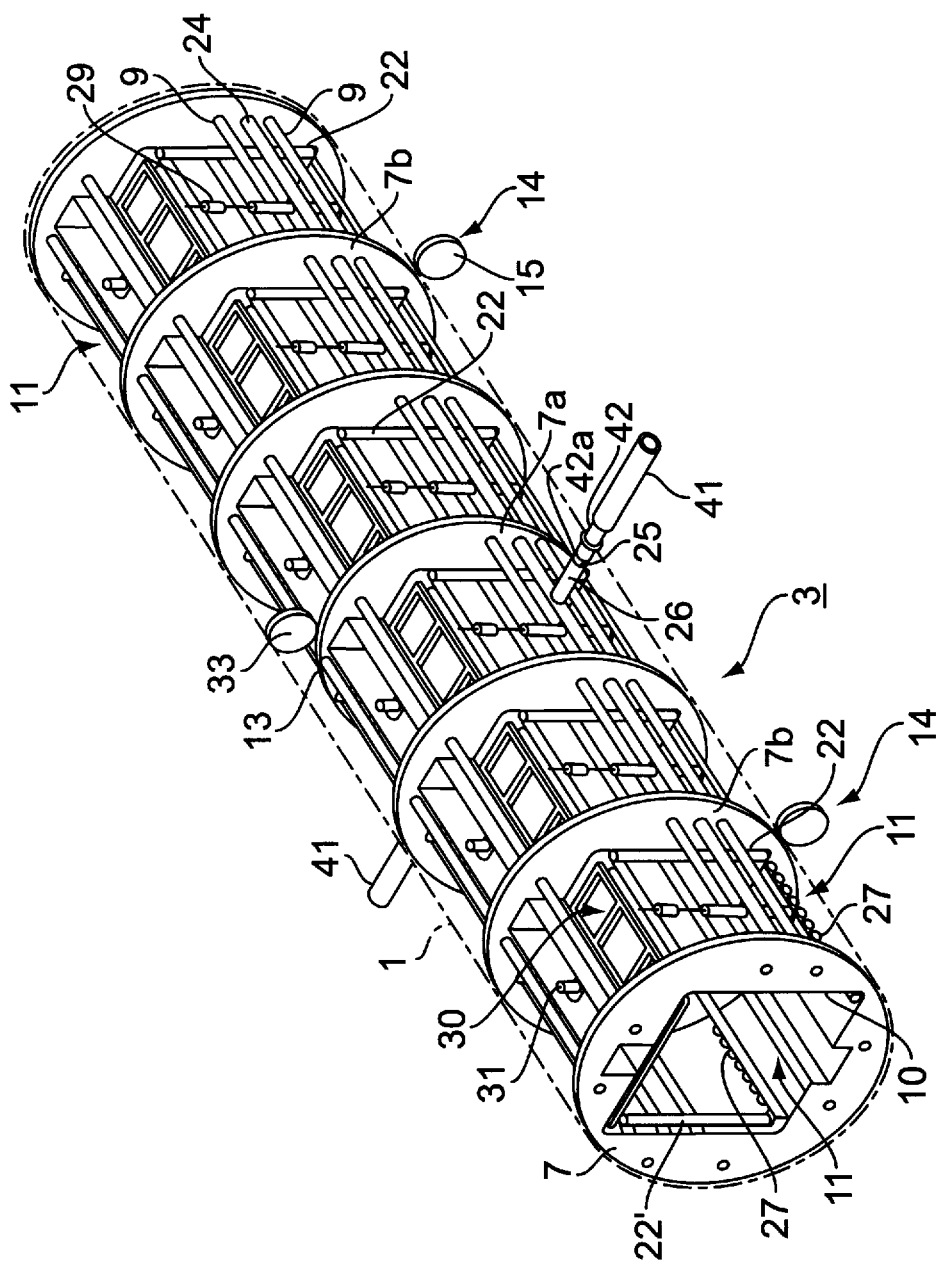
FIG. 2 is a perspective view illustrating a rotary housing.

As shown in FIG. 2, the rotary housing 3 includes a plurality (seven, for example) of rotary plates 7 of a disc-shaped configuration. The rotary plates 7 are arranged In parallel relative to one another and spaced apart from one another a distance substantially equal to the length of the tray 2. A plurality of connection members 9 of a rod-like configuration extend through the rotary plates 7 at points adjacent the outer peripheral portions thereof and fixed thereto. Each rotary plate 7 is formed with an opening 10 of a substantially rectangular configuration for permitting passage of the stacked trays 2 therethrough. The stacked trays 2 are accommodated with a space defined by the adjoining rotary plates 7 and the connection member 9. The stacked trays 2 are to be sterilized, cooled and dried while they are accommodated within the above space This space will be referred to as a "tray accommodation section" hereinbelow.

The centrally located rotary plate 7a (the driving rotary plate) is formed with a toothed portion 13 in its outer periphery. The toothed portion 13 is formed into an arcuate configuration and protrudes radially outwardly just beyond the outer peripheral surface of the driving rotary plate 7a. The central angle (the angular extension) of the arcuate toothed portion 13 is set at an angle of 90 degrees or more (in the illustrated embodiment, the central angle being set at 120 degrees: see FIG. 7). A central angle of less than 90 degrees may be used when sufficient dewatering effects could be expected.

The rotary housing 3 is supported by four support devices 14 each having a roller 15 so that it may be rotated about a horizontal axis of rotation. One pair of support devices 14 are positioned below the rotary plate 7b (supporting rotary plate) which is next to the forward-most (inlet side) rotary plate 7, and the other pair of support devices 14 are positioned below the rotary plate 7b (supporting rotary plate) which is next to the rearward-most (outlet side) rotary plate 7. Each pair of support devices 14 are disposed on opposite sides of the axis of rotation of the rotary housing 3 and in contact with the corresponding rotary plate 7b for supporting it.

Figure 3:
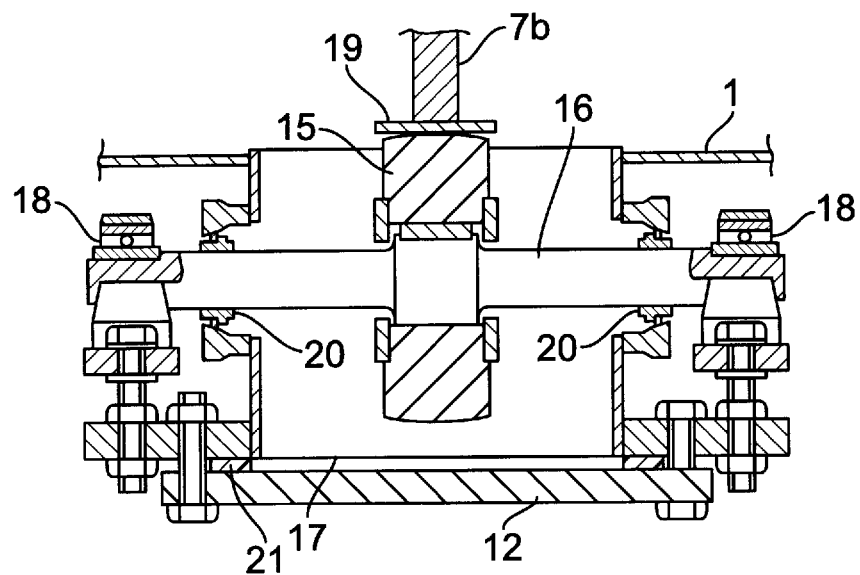
FIG. 3 is a cross-sectional view illustrating a support device.

As shown in FIG. 3, the pivot shaft 16, extending through the roller 15 at its central portion, extends through the opposite side surfaces of a case 17 mounted on the sterilization vessel 1 in its outer circumferential surface. The opposite ends of the pivot shaft 16 are rotatably supported by a respective bearing 18 mounted externally of the case 17. The outer diametrical surface of the roller 15 protrudes slightly into the sterilization vessel 1, to be in contact with an annular contact plate 19 mounted around the entire peripheral surface of the rotary plate 7. The space between the pivot shaft 16 and the case 17 is sealed by means of a seal member 20. The bottom opening of the case 17 is sealingly closed by a blind plate 12 through a gasket 21, so that any fluid such as hot water or cooling water collected in the sterilization vessel 1 at its bottom is prevented from flowing out of the sterilization vessel 1.

Figure 4:
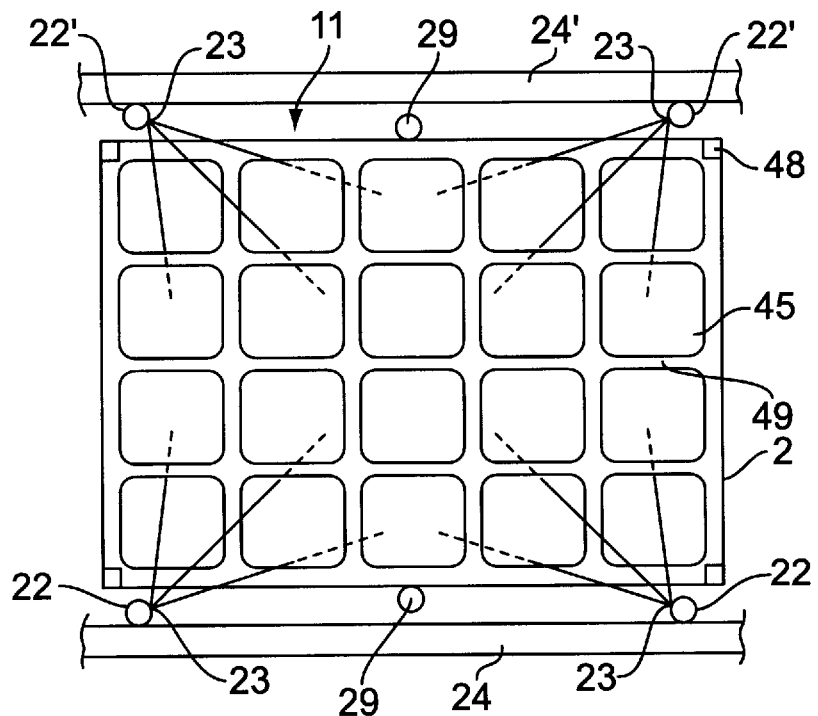
FIG. 4 is a plan view illustrating a plurality of trays accommodated within a tray accommodation section.
Figure 5:
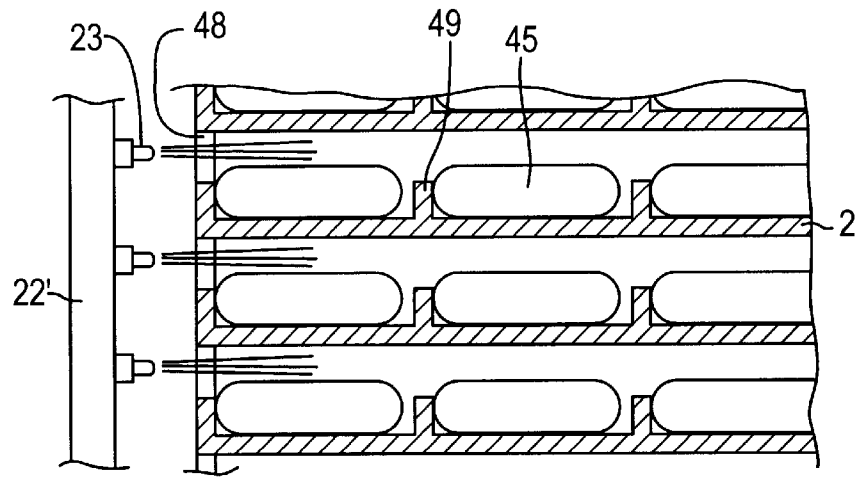
FIG. 5 is a cross-sectional view illustrating a plurality of trays accommodated within the tray accommodation section.
Figure 6:
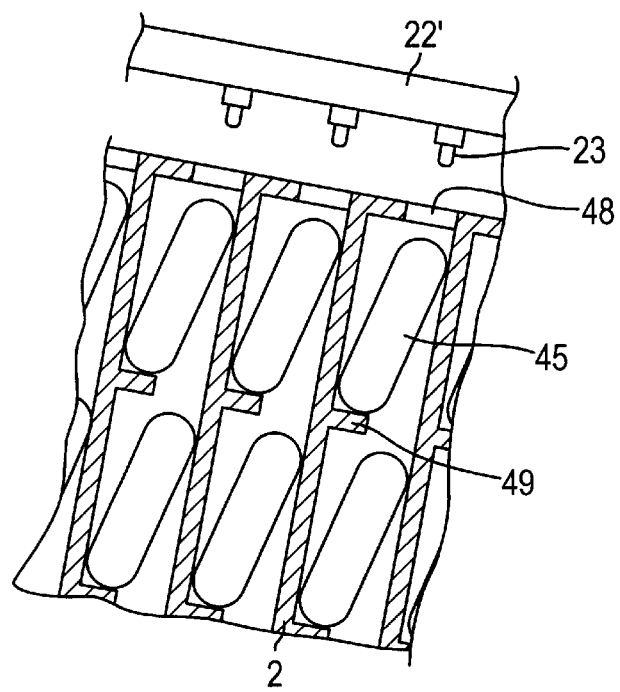
FIG. 6 is a cross-sectional view illustrating the tray accommodation section when the rotary housing is overhung.

As shown in FIG. 4, a header conduit 22 or 22' extends vertically from each of the four corners of each of the tray accommodation section 11. Each of the header conduit 22 or 22' includes a plurality of spray nozzles 23 directed toward the center of the tray 2. The spray nozzles 23 are equally spaced in the vertical direction so that they can provide a spray into a respective space between the stacked trays 2, as shown in FIG. 5.

As shown in FIGS. 2 and 4, each of the header conduits 22 or 22' is connected with a pair of connection conduits 24 and 24' extending along the entire length of the opposite sides of the rotary housing 3. The right-hand side (when viewed from the inlet side) connection conduit 24 is in communication with the header conduit 22 at the right-hand side of each of the tray accommodation sections 11, while the left-hand side (when viewed from the inlet side) connection conduit 24' is in communication with the header conduit 22' at the left-hand side of each of the tray accommodation sections 11. Each connection conduit 24 or 24' includes an Inlet conduit 26 at its central portion. The inlet conduit 26 includes an inlet port 25 directed outwardly from the sterilization vessel 1.

As shown in FIGS. 1 and 2, the stack of trays 2 contained within each tray accommodation section 11 is supported at its lower surface by a plurality of rollers 27 rotatably mounted to the lower portion of the rotary housing 3. The rollers 27 are arranged in a pair of two left-hand and right-hand rows along the entire length of the rotary housing 3. The support surface defined by the pair of roller rows is coplanar with a conveying surface of a conveyer (not shown) connected between the inlet side and the outlet side of the sterilization vessel 1.

A plurality of guide rollers 29 having a vertical axis of rotation are disposed inwardly of the connection members 9 on the opposite sides of each of the tray accommodation sections 11. The guide rollers 29 are adapted to be In contact with the opposite sides of the stacks of trays 2, to restrict and position each tray 2 the transverse direction.

A tray presser 30 is disposed above each of the tray accommodation sections 11. The tray presser 30 is formed into a lattice like configuration and moved in the vertical direction by means of a drive cylinder 31 disposed above the tray presser 30. Any mechanism for moving the tray presser in the vertical direction, such as a combination of a ball screw and a ball nut, may be used as a drive source for the tray presser 30, instead of the hydraulic cylinder.

A rotary drive unit 32 (an electric motor, for example) is mounted on the sterilization vessel 1 at its upper portion, in order to reversibly rotating the rotary housing 3. A small gear 33 is mounted on the output shaft of the rotary drive unit 32. The small gear 33 meshes with the toothed portion 13 of the driving rotary plate 7a. The driving rotary plate 7a and the entire rotary housing 3 (including the header conduits 22, 22', the connection conduits 24 and 24', the inlet conduit 26, the rollers 27 and the guide rollers 29) are rotated in unison in the forward or reverse direction, when the rotary drive unit 32 is rotated in the forward or reverse direction.

A hot air supply device 34 is disposed above the sterilization vessel 1. The hot air supply device 34 causes air flow supplied therein through a suction filter 38 and a forcing blower 39 to be heated by means of a hot air generator 35 so as to provide hot air. The hot air is supplied through a hot air supply conduit 36 and a rising conduit 37 into the sterilization vessel 1. The rising conduit 37 is slidably received within the downstream end of the hot air supply conduit 36 and is vertically moved by means of a drive unit (not shown). The rising conduit 37 includes, at its downstream end, a hot air supply port 37a which is sealingly engageable with the inlet port 25. The hot air supply port 37a may be extended into the inside of the sterilization vessel 1 through a through hole in the wall of the sterilization vessel 1 when the rising conduit 37 is lowered.

As shown in FIG. 2, the sterilization vessel 1 is provided with a pair of medium supply conduits 41 on the opposite sides of its central portion. The medium supply conduits 41 extend in the horizontal direction.

A slide conduit 42 is slidably received within the downstream end of each of the medium supply conduits 41. The slide conduit 42 is adapted to be driven by means of a drive unit (not shown) for slidable movement in the horizontal direction. Each of the slide conduits 42 is provided, at its downstream end, with a medium supply port 42a which is sealingly engageable with the inlet port 25. As with the hot air supply port 37a. the medium supply port 42a may be extended into the inside of the sterilization vessel 1 through a through hole in the wall of the sterilization vessel 1, when the slide conduit 42 is advanced.

The hot air supply port 37a and the medium supply ports 42a are spaced from one another in a plane containing the locus of revolution presented by the inlet port 25. The medium supply ports 42a are arranged in diametrically opposed relationship in a horizontal plane. The hot air supply port 37a is disposed at a position intermediate between the medium supply ports 42a (i.e., a position offset 90 degrees from each of the medium supply ports).

Figure 7A:
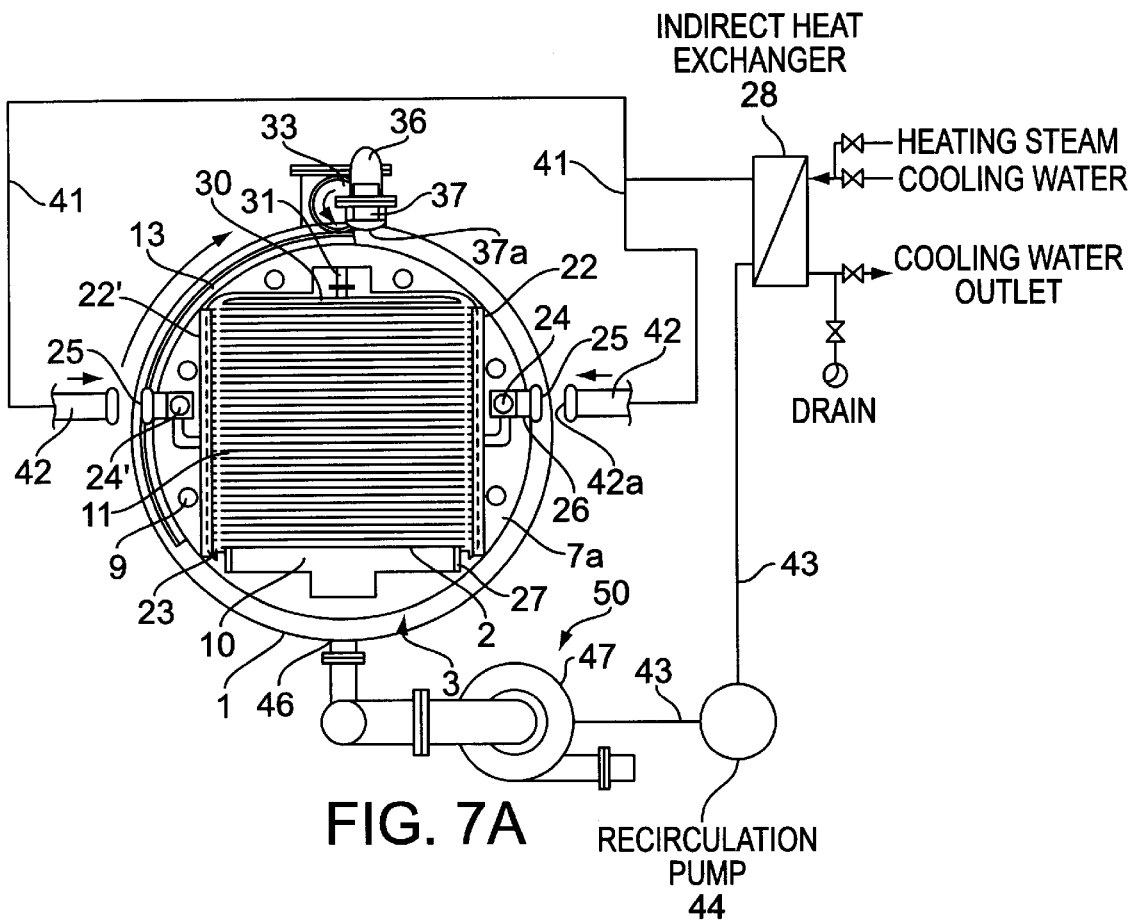
FIGS. 7A and 7B are a cross-sectional view illustrating a sterilizing/drying process performed by the apparatus according to the invention.

The upstream end of each of the medium supply conduits 41 is merged into a single piping, as shown in FIG. 7a, to be connected with a medium supply device for selectively supplying a flow of heating medium or cooling medium, such as an indirect heat exchanger 28. The indirect heat exchanger 28 is connected, at one end thereof, with a supply conduit for selectively supplying cooling water or heating steam. By selectively supplying a flow of cooling water or heating stream into the indirect heat exchanger, it is possible for the medium (water, for example) flowing through the medium supply conduit 41 to be appropriately heat-exchanged, so that a flow of heating medium (hot water) or cooling medium (cooling water) may be produced. The hot water or cooling water flowing through the medium supply conduit 41 is introduced into the sterilization vessel 1 through the slide conduit 42, the medium supply ports 42a and the inlet port 25 for the purpose of heat-sterilizing or cooling of products. A quantity of medium collected within the sterilization vessel 1 at its bottom is recovered by a return conduit 43 through discharge port 46 located at the bottom of the sterilization vessel 1 and circulated to the other end of the indirect heat exchanger 28 through a recirculation pump 44. The thus circulated medium is heat-exchanged in the indirect heat exchanger 28 and then recycled to the medium supply conduit 41.

The operational procedure of the invention will be explained below with reference to FIGS. 7a and 7b.

The closure 4 at the inlet side is opened, while the closure 5 at the outlet side is closed. A plurality of stacks of trays 2, with the trays oriented in the horizontal direction, are sequentially supplied into the rotary housing 3 by means of the transportation conveyer (not shown). When a single stack of trays 2 is accommodated in each of the tray accommodation section 11, the closure 4 at the inlet side is closed, whereby the sterilization vessel 1 is sealingly closed. Then, the drive cylinders 31 are actuated to cause the tray-pressers 30 to be lowered, whereby the stacked trays 2 are downwardly urged. It is noted that a predetermined gap may be maintained between the adjoining trays 2 by means of guides 48 upstanding from each corner of each of the trays 2 (see FIGS. 4 and 5).

Then, the slide conduit 42 is advanced to cause the medium supply ports 42a to be sealingly in contact with the respective inlet ports 25. Thereafter, the medium support conduits 41 are opened, to supply a flow of hot water heated in the indirect heat exchanger 28 into the inlet ports 25 through the medium supply ports 42a. The thus supplied hot water flows to each of the header conduits 22, 22' through the inlet conduits 26 and the connection conduits 24, 24', and then is sprayed from the spray nozzles 23 onto the products supported on the trays 2 for heat sterilization thereof. The hot water is then heated in the indirect heat exchanger 28 and recycled to the sterilization vessel 1 through the medium supply conduits 41, as mention above.

After a predetermined period of time, the indirect heat exchanger 28 is changed to its cooling mode to cause the hot water to be cooled. The thus produced cooling water is supplied to the inlet ports 25 through the medium supply conduits 41 and the medium supply ports 42a. The cooling water supplied to the inlet ports 25 is sprayed from the spray nozzles 23, to cause the products to be cooled (cooling process) to a predetermined temperature (60 degrees Celsius, for example). Thus, the packed material within the container (retort pouches or transfusion bags, for example), having been heated and pressurized in the heat sterilizing process, may be cooled and depressurized for the purpose of restricting its degradation.

When the cooling process has been completed, a discharge valve is opened to cause the cooling water remaining in the sterilization vessel 1, the medium supply conduits 41 and the return conduit 43 to be discharged from the sterilization vessel (drainage of water). Substantially at the same time, the slide conduits 42 are retracted.

Then, the rotary drive unit 32 is actuated, to cause the rotary housing 3 to be rotated in the clockwise or right-hand direction when viewed from the inlet side. By this, most of the cooling water remaining on the trays 2 and the products 45 is dropped therefrom. The stacked trays 2 are also rotated in the same direction when the rotary housing 3 is being rotated. It is noted, however, that such stacked trays 2 will not crumble, since they are tightly clamped together by means of the tray-pressers 30. It is also noted that a plurality of walls 49 protrude from the upper surface of each of the trays 2. The walls are arranged to encircle or surround the products 45 on the trays 2 for restricting movement of the products 45 (see FIGS. 4 and 5). Thus, the products 45 are prevented from moving downwardly.

The rotational movement of the rotary housing 3 is continued until the trays 2 are inclined at an angle of 120 degrees (over-hanging process) beyond their vertical position. By this, the products 45 are moved to an inclined position, whereby the lower surface of each of the products 45 is spaced from the surface of the respective trays 2. This condition is maintained for an appropriate period of time, so that water remaining between the confronting surfaces of the products 45 and the trays 2 may be removed and dried by means of heat remaining in the products 45 and the trays 2.

Figure 7B:
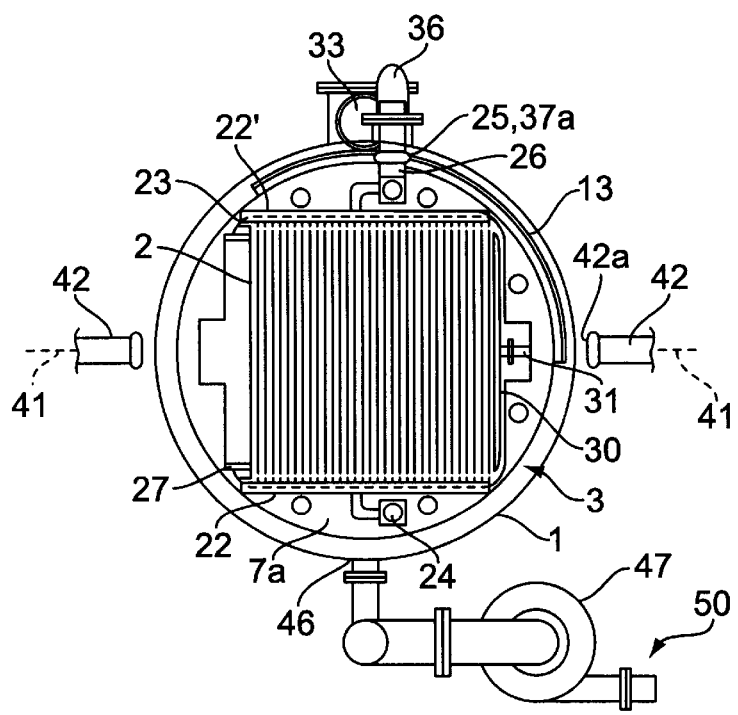
Figure 8:
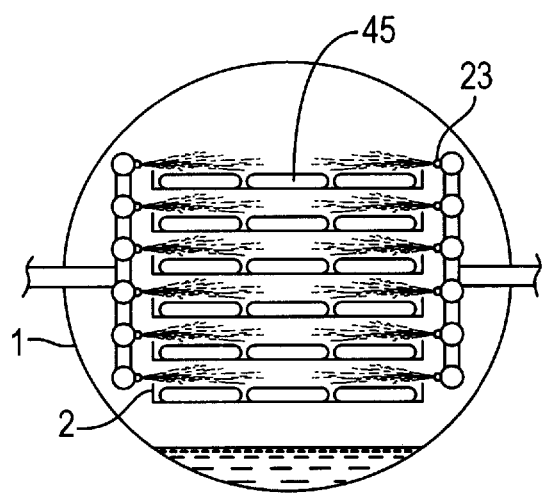
FIG. 8 is a cross-sectional view illustrating a spray sterilization apparatus in prior art.

Then, the rotary drive unit 32 is actuated in a reverse direction, to cause the rotary housing 3 to be counter-rotated until the trays 2 are oriented in a completely vertical direction, as shown in FIG. 7b. By this, one of the inlet ports 25 (upper one) comes to a position confronting to the hot air supply port 37a. Then, the movable rising conduit 37 is lowered to cause the hot air supply port 37a and the one inlet port 25 to be sealingly contacted with each other. Thereafter, the hot air supply conduit 36 is opened to supply hot air into the inlet port 25. The thus supplied hot air flows into each header conduit 22, 22' through the inlet conduit 26 and the connection conduits 24, 24'. Then, the hot air is ejected from the spray nozzles 23, to cause any water remaining on the products 45 and trays 2 to be completely dried. The spent hot air is discharged from the sterilization vessel 1 through the discharge port 46 by means of an exhaust device 50 including an exhaust blower 47.

Preferably, a plurality of discharge ports 46 are disposed at positions confronting to the hot air supply port 37a, i.e., at the lower portion of the sterilization vessel 1, so as to facilitate smooth passage of the hot air through the gas between the trays 2. According to the illustrated embodiment, the discharge port 46 serves as an outlet for the medium such as hot water and an outlet for the hot air. No spent medium flows into the exhaust blower 47 during drying process by means of the hot air, since dewatering operation is performed beforehand. It is preferable, however, that, since a small amount of water remaining in the piping is expected to flow into the exhaust blower 47, a mist separator be provided between the discharge port 46 and the exhaust blower 47.

After a predetermined period of time, supply of the hot air is stopped. Then, the rotary drive unit 32 is re-actuated, to cause the rotary housing 3 to be returned to the initial position (a position at which the trays 2 are oriented in the horizontal direction). Thereafter, the closure 5 at the outlet side is opened in order to remove the stacked trays 2 from the tray accommodation sections 11, for transportation thereof onto the conveyer (not shown). Then, the closure 5 is closed, while the closure 4 at the inlet side is opened in order to accommodate new trays in the rotary housing 3. The above procedure will be similarly repeated.

It is noted that, in the above processes, the over-hanging of the rotary housing 3 is performed only when a quantity of water or moisture remaining on the lower surfaces of the products is problematic. Otherwise, the over-hanging operation may be obviated. In such a case, the rotary housing 3 is rotated 90 degrees in order to perform drying operation by means of hot air, immediately after the cooling operation has been completed.

In accordance with the apparatus of the invention, the sterilizing operation and the drying operation may be performed in the same apparatus. This contributes to miniaturization of the sterilizing/drying line, thus permitting efficient utilization of space. The products 45 may be removed from the sterilization vessel 1 in a dried condition. This eliminates provision of counter-measure against remaining water external to the sterilization vessel, such as drainage pan or drainage trough. The problem of causing adhesion of foreign material to the products when they are wet may be eliminated. It is particularly noted that the present apparatus permits drying operation when the trays 2 are vertically oriented, By this, dewatering effect, as well as efficient drying operation may be expected.

When the sterilization line is disposed in a clean room, it is possible reduce the size of such clean room. Accordingly, medical transfusion bags, to which very high degree of hygienity is required, may be efficiently sterilized and dried in a small clean room, so that running cost and production cost may be reduced.

When the over-hanging operation for the rotary housing 3 is performed, moisture adhering on the contact surface between the products 45 and the trays 2 may be dried. This contributes to performing a more complete drying operation.

In the above description, although hot water is used as a heating medium for sterilization, any other heating medium such as steam may be similarly used.

We claim:

1. A spray sterilization apparatus comprising:

a sterilization vessel of a cylindrical configuration;

a rotary housing supported within the sterilization vessel for rotatable movement about a horizontal axis of rotation, the rotary housing accommodating therein a plurality of stacked trays, each of the trays being adapted to mount thereon at least one product;

a rotary drive unit for reversibly rotating the rotary housing;

a plurality of spray nozzles within the rotary housing, each of the spray nozzles being arranged to be directed to a space between the stacked trays;

an inlet port in the rotary housing, the inlet port being in communication with each of the spray nozzles;

a medium supply port and a hot gas supply port in the sterilization vessel, the medium supply port and the hot gas supply port being arranged in a plane containing the locus of revolution of the inlet port and spaced apart from one another, to be sealingly engageable with the inlet port;

means for supplying a flow of hot gas to the hot gas supply port; and means for discharging the hot gas flow having been introduced into the rotary housing from the sterilization vessel;

said inlet port sealingly engaged with the medium supply port while the trays are maintained at a horizontal orientation, so that the heating medium and the cooling medium, may be supplied to the medium supply port in that order;

means for rotating the rotary housing to cause the trays to be maintained at a vertical orientation;

whereby the inlet port is sealingly engaged with the hot gas supply port, so that hot gas may be supplied from the hot gas supplying means into the rotary housing; and the hot gas is discharged from the sterilization vessel via said hot gas discharging means.

2. A spray sterilization apparatus according to claim 1, wherein the rotary housing is adapted to be rotatable to a position in which the trays are inclined beyond the vertical orientation.

3. A method for performing spray sterilization relative to trays and products thereon comprising the steps of:

accommodating a plurality of trays having a product thereon in a stacked manner within a rotary housing disposed in a sterilization vessel of a cylindrical configuration;

injecting a spray of heating medium from a spray nozzle in the rotary housing toward the trays for heat sterilizing the products on the trays, while the trays are maintained at a horizontal orientation;

injecting a spray of cooling medium from the spray nozzle for cooling the products, while the trays are maintained at a horizontal orientation;

rotating the rotary housing so as to cause the trays to be maintained at a vertical orientation; and supplying hot air from the spray nozzle, while discharging the hot air from the sterilization vessel.

4. A method according to claim 3, wherein, after performing the step of injecting a spray of cooling medium subsequent to the step of injecting a heating medium, rotating the rotary housing to a position in which the trays are inclined further beyond the vertical orientation, maintaining the position for a predetermined period of time, and then, rotating the rotary housing so that the trays are returned to the vertical orientation for performing a drying operation by means supplying hot air.

* * * * *